United States Patent [19]
Meglasson

[11] Patent Number: 5,900,435
[45] Date of Patent: * May 4, 1999

[54] COMPOSITION, FOOD PRODUCT AND USES OF 3-GUANIDINOPROPIONIC ACID

[75] Inventor: Martin D. Meglasson, Kalamazoo, Mich.

[73] Assignee: Pharmacia & Upjohn Company, Kalamazoo, Mich.

[ * ] Notice: This patent is subject to a terminal disclaimer.

[21] Appl. No.: 08/196,250

[22] PCT Filed: Aug. 19, 1992

[86] PCT No.: PCT/US92/06776

§ 371 Date: Feb. 24, 1994

§ 102(e) Date: Feb. 24, 1994

[87] PCT Pub. No.: WO93/03724

PCT Pub. Date: Mar. 4, 1993

Related U.S. Application Data

[63] Continuation-in-part of application No. 07/751,239, Aug. 26, 1991, and a continuation-in-part of application No. 07/750,559, Aug. 26, 1991, abandoned.

[51] Int. Cl.$^6$ ............................. A61K 31/195; A23L 1/00
[52] U.S. Cl. .......................... 514/565; 514/866; 514/909; 426/330; 426/330.5
[58] Field of Search ..................................... 514/330, 369, 514/565, 592, 909, 866; 426/330, 330.5

[56] References Cited

U.S. PATENT DOCUMENTS

| | | | |
|---|---|---|---|
| 3,843,798 | 10/1974 | Cook et al. ............................. | 424/319 |
| 5,053,420 | 10/1991 | Pershadsingh et al. ................. | 514/369 |
| 5,132,324 | 7/1992 | Meglasson ............................... | 514/565 |
| 5,134,164 | 7/1992 | Meglasson ............................... | 514/565 |

FOREIGN PATENT DOCUMENTS

| | | |
|---|---|---|
| 0445920 A2 | 9/1991 | European Pat. Off. . |
| 1195199 | 11/1966 | United Kingdom . |
| 1195200 | 2/1967 | United Kingdom . |
| 1552179 | 11/1976 | United Kingdom . |
| 91/07954 | 6/1991 | WIPO . |
| 91/12799 | 9/1991 | WIPO . |
| WO 91/12800 | 9/1991 | WIPO . |

OTHER PUBLICATIONS

EA Shoubridge, et al., "Biochemical adaptation in the skeletal muscle of rats depleted of creatine with the substrate analogue β–guanidinopropionic acid", Biochem. J. 232: 125–131, 1985.

TS Moerland, et al., "Administration of a creatine analogue induces isomyosin transitions in muscle", Am. J. Physiol. 257: C810–816, 1989.

DA Mahanna, et al., "Effects of β–Guanidinopropionic Acid on Murine Skeletal Muscle", Exper. Neurol. 68: 114–121, 1980.

RP Shields, et al., "Skeletal Muscle Function and Structure after Depletion of Creatine", Lab Invest. 33: 151–158, 1975.

JV Otten, et al., "Thyrotoxic Myopathy in Mice: Accentuation by a Creatine Transport Inhibitor", Metabolism vol. 35, No. 6 (pp. 481–484) 1986.

Medline, Holtzman et al., "Brain creatine phosphate and creatine kinase in mice fed an analogue of creatine", see abstract No. 89208225, Brain Res., 483(1), 68–77.

Chemical Abstracts 112:172124r (1990).

Chemical Abstracts 113:71079v, Y. Sugiyama, et al., "Effects of pioglitazone on glucose and lipid metabolism in Wistar rats.", Arzneim. Forsch., vol. 40, No. 3, pp. 263–267 (1990).

Chemical Abstracts 114:240370m (1990).

R. P. Shields and C. K. Whitehair, "Muscle creatine: In vivo depletion by feeding β–guanidinopropionic acid", Can J. Biochem., 51:1046–1049 (1973).

E. A. Shoubridge et al., "Creatine kinase kinetics, ATP turnover, and cardiac performance in hearts depleted of creatine with the substrate analogue β–guanidinopropionic acid", Biochim. Biophys. Acta. 847:25–32 (1985).

Primary Examiner—Kevin E. Weddington
Attorney, Agent, or Firm—Martha A. Gammill; Lucy X. Yang

[57] ABSTRACT

The present invention provides a new composition, food product and uses for a known compound. More particularly, the present invention provides a new pharmaceutical composition containing 3-guanidinopropionic acid and a method of using 3-guanidinopropionic acid to prevent or treat obesity in non-insulin dependent diabetic (NIDDM) patients that is caused by treatment with anti-diabetic drugs, such as an insulin sensitizing drug or an insulin secretion stimulating drug. Examples of insulin sensitizing drugs are pioglitazone and pioglitazone hydrochloride. Examples of insulin secretion stimulating drugs are glyburide and glimepiride. The present invention also provides a new food product containing 3-guanidinopropionic acid and a method of using 3-guanidinopropionic acid to increase endurance, stamina and exercise capacity.

3 Claims, 1 Drawing Sheet

COMPOSITION, FOOD PRODUCT AND USES OF 3-GUANIDINOPROPIONIC ACID

This application is the national phase of international application PCT/US92/06776, filed Aug. 19, 1992, which is a continuation-in-part of U.S. application Ser. No. 07/751,239, filed Aug. 26, 1991, now issued, and U.S. application Ser. No. 07/750,559, filed Aug. 26, 1991, now abandoned.

FIELD OF INVENTION

The present invention provides a new composition, food product and uses for a known compound. More particularly, the present invention provides a new pharmaceutical composition containing 3-guanidinopropionic acid and a method of using 3-guanidinopropionic acid to prevent or treat obesity in non-insulin dependent diabetic (NIDDM) patients that is caused by treatment with anti-diabetic drugs, such as an insulin sensitizing drug or an insulin secretion stimulating drug. Examples of insulin sensitizing drugs are pioglitazone and pioglitazone hydrochloride. Examples of insulin secretion stimulating drugs are glyburide and glimepiride. Furthermore, the present invention provides a new food product containing 3-guanidinopropionic acid and a method of using 3-guanidinopropionic acid to increase endurance, stamina and exercise capacity.

BACKGROUND

There are several metabolic disorders of human and animal metabolism, e.g., hyperglycemia, impaired glucose tolerance, hyperinsulinemia and insulin insensitivity, hyperamylinemia, excess adiposity, and hyperlipidemia. Some or all of the above disorders may occur in the following disease states: non-insulin dependent diabetes mellitus (NIDDM), obesity, hypertension and atherosclerosis.

Hyperglycemia is a condition where the blood glucose level is above the normal level in the fasting state, following ingestion of a meal, or during a provocative diagnostic procedure, e.g., a glucose tolerance test. It can occur in NIDDM as well as obesity. Hyperglycemia can occur without a diagnosis of NIDDM. This condition is called impaired glucose tolerance or a pre-diabetes. Impaired glucose tolerance occurs when the rate of metabolic clearance of glucose from the blood is less than that commonly occurring in the general population after a standard dose of glucose has been orally or parenterally administered. It can occur in NIDDM as well as obesity, pre-diabetes and gestational diabetes.

Hyperinsulinemia is defined as having a blood insulin level that is above normal level in the fasting state, following ingestion of a meal or during a provocative diagnostic procedure. It can be seen in NIDDM or obesity and can be associated with or causal in hypertension or atherosclerosis. Hyperinsulinemia can occur without a diagnosis of diabetes. It may occur prior to the onset of NIDDM. Insulin insensitivity, also called insulin resistance, occurs when the insulin-dependent glucose clearance rate is less than that commonly occurring in the general population during diagnostic procedures such as a hyperinsulinemic clamp [See, e.g., DeFronzo, R. A. et al., Am. J. Physiol. 232:E214–E233, (1979)] or a minimal model test. See, e.g., Bergman, R. N. et al., J. Clin. Invest. 68:1456–1467 (1981). Insulin insensitivity is considered also to occur when the blood glucose concentration is higher than that commonly occurring in the general population after intravenous administration of insulin (insulin tolerance test) or when the ratio of serum insulin-to-glucose concentration is higher than that commonly occurring in the general population after a 10–16 hour fast. Insulin insensitivity may be found in NIDDM or obesity and can also be associated with or causal to hypertension or atherosclerosis.

Hyperamylinemia is defined as having an abnormally high blood amylin level. Amylin is also known as diabetes associated peptide (DAP) and insulinoma associated polypeptide (IAP). Hyperamylinemia can be seen in NIDDM or obesity.

Excess adiposity can be seen in NIDDM associated with obesity as well as obesity without NIDDM. It is defined as a higher fat body mass-to-lean body mass ratio than that commonly occurring in the general population as measured by whole body specific gravity or other generally accepted means.

Hyperlipidemia is defined as having an abnormal level of lipids in the blood. Hyperlipidemia exists when the serum concentration of total cholesterol or total triglycerides or the serum concentration of LDL-cholesterol/HDL-cholesterol is higher than that commonly occurring in the general population. It can be seen in NIDDM or atherosclerosis.

The above disease states could be treated by either ameliorating or preventing the metabolic and biochemical disorders. In addition, humans and animals, which have not been diagnosed as having one of the above disease states but evidencing some or all of the disorders described above, could be benefitted by preventing the development of a currently recognized disease state. Therefore, a compound that is useful in the treatment of hyperglycemia, impaired glucose tolerance, hyperinsulinemia, insulin insensitivity, hyperamylinemia, excess adiposity or hyperlipidemia could also be used to treat or prevent NIDDM, obesity, hypertension or atherosclerosis.

3-Guanidinopropionic acid (3-GPA) is an endogenous metabolite found in animals and humans. See, e.g., Hiraga, Y. et al., J. Chromatography 342:269–275 (1985) and Watanabe, Y. et al., Guanidines, edited by Mori et al., Plenum, N.Y., pp. 49–58 (1983). The compound, which is available from Sigma Chemical Co., has been used extensively in the study of creatine metabolism [See, e.g., Walker, J. B., Adv. Enzymol. 50:177–242 (1979)] and gamma-aminobutyric acid receptor function. See, e.g., Bowery, R. et al., Br. J. Pharmacol. 50:205–218 (1974). Except as noted below, these studies do not relate to 3-GPA's utility in treating human or animal disease.

Guanidine, monoguanidine and diguanidine compounds have been shown to produce hypoglycemia. See, e.g., Watanabe, C., J. Biol. Chem. 33:253–265 (1918); Bischoff, F. et al., Guanidine structure and hypoglycemia 81:325–349 (1929). However, these compounds were observed to be toxic. In 1957, biguanide derivatives, e.g. phenformin and metformin, were used clinically as anti-diabetic agents. Some members of this class continue to be used today while others have been withdrawn from the market or banned in the United States and most Western countries. See, e.g., Schafer, G., Diabete Metabol. (Paris) 9:148–163 (1983).

Gamma-guanidinobutyramide also known as Tyformin, and the HCl salt of Tyformin, known as Augmentin, were investigated as potential anti-diabetic agents from the mid-1960's until the mid-1970's. While Augmentin produced hypoglycemia, it was reported to produce hypertension in dogs [See, e.g., Malaisse, W. et al., Horm. Metab. Res. 1:258–265 (1969)] and respiratory and circulatory collapse in rats and rabbits. See, e.g., Buckle, A. et al., Horm. Metab. Res. 3:76–81 (1971). The free acid of the amide was said to lack hypoglycemic activity [See, e.g., Beeson, M. et al., Horm. Metab. Res. 3:188–192 (1971)].

British patent 1,153,424 discloses the use of certain esters and amides of guanidinoaliphatic acids in the treatment of diabetes mellitus where hyperuremia is present. The patent does not disclose that these compounds have an effect on hyperglycemia or any other symptom or pathological state related to diabetes. In Canadian patent, 891509, the use of esters and amides of guanidinoaliphatic acids were disclosed for treating hyperuremia and hyperglycemia in diabetes mellitus. As noted above, the biologic activity of a guanidino alkanoic acid was known to be different and less favorable so as to be ineffective compared to its amide for treating hyperglycemia.

British patent, 1,195,199 discloses the use of guanidino alkanoic acids or their amides or esters in an insulin-containing, parenterally-administered composition for the treatment of hyperglycemia occurring in diabetes mellitus of the type where the pancreas produces insufficient insulin. According to this patent, the combining of a guanidino alkanoic acid, amide or ester with insulin reduces the risk of hypoglycemia as compared to insulin alone. British patent 1,195,200 discloses the use of guanidino alkanoic acids in a composition containing a guanidino alkanoic acid amide or ester derivative for the treatment of hyperglycemia occurring in diabetes mellitus of the type where the pancreas produces insufficient insulin. The subsequent British patent 1,552,179 discloses the use of guanidino alkanoic acids, their salts, amides or esters in combination with a gluconeogenesis inhibitor for treating hyperglycemic conditions, such as in the type of diabetes mellitus described above. Metformin was cited as an inhibitor of gluconeogenesis. Biological data indicated that HL 523, the preferred guanidino alkanoic acid derivative, was inactive as a single agent in six of seven experiments where blood glucose concentration was measured in alloxan diabetic mice and only weakly active in the seventh study.

Tables 5, 6 and 8 of the '179 patent disclose data which show that no straight chained guanidinoalkanoic acids were active when tested for hypoglycemic activity in alloxan diabetic mice. (Compounds which produced a significant change in blood glucose are denoted by asterisks (*) in these tables.) In Table 5, compound HL 6450 (4-guanidinobutyric acid) was inactive when administered alone. In Table 6, compounds HL 6416 (guanidinovaleric acid), HL 6450 (4-guanidinobutyric acid), HL 6439 (5-guanidinovaleric acid) and HL 6361 were inactive when administered alone. In Table 8, compound HL 6450 (4-guanidinobutyric acid) was slightly active at 2 hours and inactive at 4 hours. However, this slight activity contradicts the findings in Tables 5 and 6. These data showing inactivity of guanidinoalkanoic acids as single agents for lowering blood glucose concentration are supported by the assertion of Beecham Research Laboratories' agents that while 4-guanidinobutyramide "when given to animals in high doses (600 mg/kg sucutaneously in rats) it is hypoglycemic; the free acid (HL 521) lacks this property." (M. F. Beeson et al., (1971) "E.H.: Studies on the metabolism of gamma-guanidinobutyric acid (HL 521) and its amide (HL 523)" Horm. Metab. Res. 3: 188–192.)

The British patents '199, '200 and '179 do not claim utility for guanidino alkanoic acids, as the sole active component, in compositions for treating hyperglycemic symptoms in diabetes. As described above, among the guanidino alkanoic acids tested, several were inactive as a single agent. Thus, a variety of guanidino alkanoic acids lack significant anti-diabetic activity and combination of these compounds with an agent of known anti-diabetic activity, e.g., metformin, is necessary to show beneficial activity.

Furthermore, these patents do not disclose the use of 3-guanidinopropionic acid (3-GPA) to prevent or treat iatrogenic obesity or any other form of obesity. Also, these patents provide no teaching or suggestion of a food product containing 3-GPA.

Aynsley-Green and Alberti injected rats intravenously with 3-GPA, arginine, guanidine, 4-guanidinobutyramide, and 4-guanidinobutyric acid. Arginine and 3-GPA stimulated insulin secretion transiently, but did not affect the blood glucose concentration while the other compounds stimulated insulin secretion but produced a rise in blood glucose concentration. See, e.g., Aynsley-Green, A. et al., Horm. Metab. Res. 6:115–120 (1974). Blachier, et al., observed that 10 mM 3-GPA stimulated insulin secretion by isolated rat islets in vitro. See, e.g., Blachier, F. et al., Endocrinology 124:134–141 (1989). The insulin response induced by 3-GPA was 55% of that occurring when arginine was tested at the same concentration. In rats fed a diet supplemented with 10 mg/g 3-GPA for 30–60 days, the heart glycogen content was increased. See, e.g., Roberts, J. et al., Am. J. Physiol. 243:H911-H916 (1982). Similarly, skeletal muscle glycogen content was increased in rats fed chow supplemented with 10 mg/g of 3-GPA for 6–10 weeks. Mice fed a diet supplemented with 3-GPA at 20 mg/g and supplied with drinking water containing 5 mg/ml 3-GPA for 7–12 weeks had serum glucose concentrations that did not differ significantly from mice receiving unsupplemented chow and water. See, e.g.,:Moerland, T. et al., Am. J. Physiol. 257:C810–C816 (1989).

With respect to adiposity, it is known that in some, but not all cases [See, e.g., Shoubridge, E. et al., Biochem. J. 232:125–131 (1985)], supplementation of the diet with 10–20 mg/g 3GPA results in decreased body weight. See, e.g., Moerland, supra and Mahanna, D. et. al., Exper. Neurol. 68:114–121 (1980). This effect has been attributed to decreased skeletal muscle mass and has not been attributed to reduced adiposity or decreased lipid storage. See, e.g., Mahanna, supra and Shields, R. et al., Lab. Invest. 33:151–158 (1975); and Otten et al.: Thyrotoxic Myopathy in Mice: Accentuation by a Creatine Transport Inhibitor. Metabolism. Vol. 35, No. 6, (pages 481–484, 1986).

Therefore, what is needed in the art is a therapy that may be used in combination with anti-diabetic drugs to treat or prevent obesity, resulting from treatment with an insulin sensitizing drug or an insulin secretion stimulating drug.

Also, patients suffering from any of the above metabolic disorders often experience lack of stamina and endurance and decreased exercise capacity. Other diseases that may result in decreased exercise ability include: diseases resulting from muscular dysfunction, such as post-poliomyelitis chronic muscle fatigue syndrome or muscular dystrophy; diseases resulting from chronic muscular weakness associated with advanced age or chronic immobilization; diseases resulting from tissue hypoxia, such as peripheral claudication, angina, myocardial infarction, and stroke; and wasting diseases, such as cancer. Therefore, what is also needed in the art is a therapy that increases endurance, stamina and exercise capacity in patients who are performing at less than optimal levels.

INFORMATION DISCLOSURE

British patent, 1,195,199 discloses the use of guanidino alkanoic acids or their amides or esters in an insulin-containing, parenterally-administered composition for the treatment of hyperglycemia occurring in diabetes. British patent 1,195,200 discloses the use of guanidino alkanoic acids in a composition containing a guanidino alkanoic acid amide or ester derivative for the treatment of hyperglycemia occurring in diabetes. In British patent, 1,552,179, the use of guanidino alkanoic acids, their salts, amides or esters in combination with an inhibitor of hepatic gluconeogenesis for treating hyperglycemic conditions was disclosed. Metformin was cited as an inhibitor of hepatic gluconeogenesis.

U.S. Pat. No. 3,843,798 discloses a method for using 3-guanidinopropionic acid to treat bacterial infections and pharmaceutical compositions useful therefor.

U.S. Pat. No. 5,134,164, issued Jul. 28, 1992, claims a method of using 3-guanidinopropionic acid (3-GPA) to treat excess adiposity. U.S. Pat. No. 5,132,324, issued Jul. 21, 1992, claims a method of using 3-GPA to treat non-insulin dependent diabetes mellitus (NIDDM). The following published PCT applications correspond to the above U.S. patents: WO 91/12800, published Sept. 5, 1991, and WO 91/12799, published Sept. 5, 1991.

It is known that in some, but not all cases (E. A. Shoubridge, R. A. J. Challis, D. J. Hayes, and G. K. Radda: Biochemical adaptation in the skeletal muscle of rats depleted of creatine with the substrate analogue β-guanidinopropionic acid. Biochem. J. 232: 125–131, 1985), supplementation of the diet with 10–20 mg/g 3-guanidinopropionic acid results in decreased body weight (T. S. Moerland, N. G. Wolf, and M. J. Kushmerick: Administration of a creatine analogue induces isomyosin transitions in muscle. Am. J. Physiol. 257: C810–816, 1989; D. A. Mahanna, C. D. Fitch, and V. W. Fischer: Effects of b-guanidinopropionic acid on murine skeletal muscle. Exper. Neurol. 68: 114–121, 1980). This effect when it occurs, has generally been attributed to decreased skeletal muscle mass and has not been attributed to reduced obesity, adiposity or lipid storage (D. A. Mahanna, C. D. Fitch, and V. W. Fischer: Effects of b-guanidinopropionic acid on murine skeletal muscle. Exper. Neurol. 68: 114–121, 1980; R. P. Shields, C. K. Whitehair, R. E. Carrow, W. W. Heusner, and W. D. Van Huss: Skeletal muscle function and structure after depletion of creatine. Lab. Invest. 33: 151–158, 1975). Otten et al.: Thyrotoxic Myopathy in Mice: Accentuation by a Creatine Transport Inhibitor. Metabolism Vol. 35, No. 6 (pages 481–484, 1986), discloses that mice fed 3-guanidinopropionic acid had a toxic effect and that the animals did not gain weight as quickly as the animals not treated with the drug. This weight loss was attributed to loss of muscle not loss of fat.

Shields, supra also indicates that 3-guanidinopropionic acid (3-GPA) results in decreased exercise tolerance in rats. And in Moerland, supra it is stated that the use of the voluntary running wheel by β-GPA-treated mice and controls was not significantly different and that β-GPA was ineffective on blood glucose when administered in food in rats in high concentration.

Chemical Abstracts (112:172124r) describes the treatment of hyperglycemia and hyperlipidemia with the oral administration of pioglitazone. Chemical Abstracts (114:240370m) describes the treatment of hyperglycemia and ketonemia with a combination of sulfonylurea antidiabetic drugs and insulin pumps. Pershadsingh et al. describes the treatment of essential hypertension with compositions of thiazolidine derivatives.

International Publication No. WO 91/07954, published Jun. 13, 1991, discloses guanidino acetic acid or its salt for administration in affectious and physical conditions which require and increase of the intracellular muscle content of creatine. 3-GPA has been shown in the art to have the opposite effect, i.e., to decrease and in some cases almost totally eliminate creatine in muscle and heart. See, for example, R. P. Shields and C. K. Whitehair, "Muscle creatine: In vivo depletion by feeding β-guanidinopropionic acid", Can.J. Biochem. 51: 1046–1049 (1973); and E. A. Shoubridge et al., "Creatine kinase kinetics, ATP turnover, and cardiac performance in hearts depleted of creatine with the substrate analogue β-guanidinopropionic acid", Biochim. Biophys. Acta 847: 25–32 (1985).

SUMMARY OF THE INVENTION

The present invention particularly provides:
A pharmaceutical composition which comprises:
  a) 3-guanidinopropionic acid or a pharmaceutically acceptable salt thereof; and
  b) an insulin sensitizing drug or an insulin secretion stimulating drug;
A method of preventing or treating obesity in a non-insulin dependent diabetic (NIDDM) patient made susceptible to or experiencing obesity as a result of treatment with an insulin sensitizing drug or an insulin secretion stimulating drug which comprises:
  the administration to the patient of an amount of 3-guanidinopropionic acid or a pharmaceutically acceptable salt thereof effective to treat or prevent obesity in addition to the insulin sensitizing drug or insulin secretion stimulating drug;
A method of increasing endurance, stamina or exercise capacity in a mammal which comprises:
  the administration to the mammal of an amount of 3-guanidinopropionic acid or a pharmaceutically acceptable salt thereof effective to increase the endurance, stamina or exercise capacity of the mammal; and
A food product which comprises:
  a) a food; and
  b) 3-guanidinopropionic acid or a pharmaceutically acceptable salt thereof in an amount effective to:
    1) increase the endurance, stamina or exercise capacity of a mammal in need thereof;
    2) treat excess adiposity in a mammal in need thereof; or
    3) treat non-insulin dependent diabetes mellitus (NIDDM) in a mammal in need thereof.

By "3-GPA" is meant 3-guanidinopropionic acid of formula I in the Formula Chart below. Pharmaceutically acceptable salts of 3-guanidinopropionic acid are described in the references cited above and are well known to and readily prepared by one of ordinary skill in the art.

By "insulin sensitizing drug" is meant a drug that will lower blood glucose levels by increasing the responsiveness of the tissues to insulin. Examples of insulin sensitizing drugs are pioglitazone, pioglitazone hydrochloride, and its analogs as described in Drugs of the Future, Volume 15, 1990, pages 1082–1083.

By "insulin secretion stimulating drug" is meant a drug that stimulates the secretion of insulin in patients. Examples of insulin secretion stimulating drugs are glyburide, glimepiride and their analogs as described in H. E. Lebovitz: Oral hypoglycemic agents, In: Ellenberg and Rifkin's Diabetes Mellitus, Theory and Practice, 4th Ed., edited by H. Rifkin and D. Porte, Jr., Elsevier, N.Y., 1990, pages 554–557.

Another class of anti-diabetic drugs is known as inhibitors of hepatic gluconeogenesis. Examples of such inhibitors are Metformin and others described in British Patent 1,552,179, page 2, line 48—page 4, line 2. Such inhibitors are specifically excluded from the above definition.

By "pharmaceutically acceptable carrier or excipient" is meant any carrier or excipient that is commonly used in pharmaceutical compositions and are well known and readily prepared by one of ordinary skill in the art. Such carrier or excipient may be a solid or liquid containing one or more suspending, dispersing, stabilizing, emulsifying, buffering, thickening, sweetening, flavoring, coloring or preservative agents.

By "Non-insulin dependent diabetes mellitus (NIDDM)," also known as Type II diabetes, is meant a condition wherein patients have an abnormally high blood glucose concentration when fasting and delayed cellular uptake of glucose following meals or after a diagnostic test known as the glucose tolerance test. NIDDM is distinguished from insulin-dependent diabetes mellitus (Type I diabetes) based on clinical symptoms, etiology, and recognized diagnostic criteria (American Diabetes Association Clinical Education Program, Physician's Guide to Non-Insulin-Dependent (Type II) Diabetes: Diagnosis and Treatment. American Diabetes Association, Alexandria, Va., 2nd Edition, 1988). Diagnostic criteria that apply exclusively to NIDDM and are distinctly different from insulin-dependent diabetes mellitus (IDDM, also known as Type I diabetes) are the following: patients are usually older than 30 years of age at diagnosis, are obese (Physician's Guide to Non-Insulin-Dependent (Type II) Diabetes: Diagnosis and Treatment, supra, pages 3–5) and have normal or elevated fasting plasma insulin levels (Physician's Guide to Non-Insulin-Dependent (Type II) Diabetes: Diagnosis and Treatment, supra, page 15).

By "Obesity" is meant a condition in which there is an increase in body fat content in excess of accepted norms for age, gender, height, and body build (E. S. Horton, and B. Jeanrenaud: Obesity and diabetes mellitus, In: Ellenberg and Rifkin's Diabetes Mellitus, Theory and Practice, 4th Ed., edited by H. Rifkin and D. Porte, Jr., Elsevier, N.Y., 1990, page 458.) Accepted norms have been determined by life insurance mortality experience and by incidence of morbidity in relation to body composition. Body fat content is determined directly by postmortem carcass composition analysis or indirectly by the body mass index or by measuring total body water or body density. For example, a body fat content >25% or >30% in men and women, respectively, is considered obese (G. A. Bray: Obesity: An endocrine perspective. In: Endocrinology, Vol. 3, edited by L. J. DeGroot, Saunders, Philadelphia, 1989, pages 2303–2306). Obesity commonly precedes NIDDM and contributes to the etiology of NIDDM by causing insulin resistance (M. F. Saad, W. C. Knowler, D. J. Pettitt, R. G. Nelson, D. M. Mott, and P. H. Bennett: N. Eng. J. Med. 319: 1500–1506, 1988; R. C. Bonadonna, L. Groop, N. Kraemer, E. Ferrannini, S. Del Prato, and R. A. DeFronzo: Obesity and insulin resistance in humans: a dose-response study. Metabolism 39: 452459, 1990; E. F. Pfeiffer, and S. S. Fajans: Non-insulin-dependent diabetes mellitus. IDF Bulletin 34: 11–13, 1989). Note, however, that not all obese patients become diabetic ((M. F. Saad, W. C. Knowler, D. J. Pettitt, R. G. Nelson, D. M. Mott, and P. H. Bennett: N. Eng. J. Med. 319: 1500–1506, 1988). Thus the disease states, while often occurring together, are distinct.

Natural or spontaneous obesity results from an energy imbalance wherein energy intake in the form of foodstuffs is chronically in excess of energy expenditure. Energy imbalance may result from excessive food intake, an abnormally low basal metabolic rate, an abnormally low thermic response to food ingestion, or an abnormally low expenditure of energy in exercise. (G. A. Bray, Obesity: An Endocrine Perspective, In: Endocrinology, Vol. 3, edited by DeGroot, Philadelphia: W. B. Saunders, 1989, pp. 2303–2337). Natural or spontaneous obesity is a disorder in which susceptibility to the disease is inherited. As an illustration, Bray, supra, is cited: "it is clear that single and polygenic modes of inheritance are both involved in the transmission of obesity in humans."

Thus natural or spontaneous obesity is distinguished from iatrogenic obesity, as it is described herein, since in the latter, obesity results from the application of an anti-diabetic drug, such as an insulin sensitizing or insulin secretion stimulating drug, and occurs even in patients receiving treatment with a low calorie diet (UK prospective study of therapies of maturity-onset diabetes. I. Effect of diet, sulphonylurea, insulin or biguanide therapy on fasting plasma glucose and body weight over one year. Diabetologia 24: 404–411, 1983).

By "patient made susceptible to or experiencing obesity as a result of treatment with an insulin sensitizing drug or an insulin secretion stimulating drug" is meant a human or animal who is receiving medical treatment for NIDDM with, for example, an insulin sensitizing drug or an insulin secretion stimulating drug, and who is at high risk for developing or has developed obesity. Such patients are readily diagnosed by a physician or veterinarian of ordinary skill.

By "treating" is meant the amelioration or total avoidance of obesity as described herein. By "preventing" is meant the avoidance of obesity, as described herein. For example, at the point of treatment with an anti-diabetic drug, such as an insulin sensitizing drug or an insulin secretion stimulating drug, 3-GPA may be used to prevent the development of iatrogenic obesity.

By "unit dose" is meant a discrete quantity of 3-GPA in a form suitable for administering for medical or veterinary purposes. Thus, an ideal unit dose would be one wherein one unit, or an integral amount thereof, contains the precise amount of 3-GPA for a particular purpose, e.g., for treating or preventing obesity resulting from treatment with anti-diabetic drugs. As would be apparent to a person of ordinary skill in pharmaceutical formulations, 3-GPA can be formulated into conventional unit doses. These unit doses can be packaged in a variety of forms, e.g., tablets, hard gelatin capsules, foil packets, glass ampules, and the like. Similarly, a unit dose may be delivered from a medicine dropper or from a pump spray. These various unit doses may then be administered in various pharmaceutically acceptable forms of liquid administration, i.e., orally or parenterally. Thus, for example, the contents of a foil packet may be dissolved in water and ingested orally, or the contents of a glass vial may be injected. Similarly, a discrete amount form a medicine dropper or a pump spray may be dissolved in water.

By "in addition to" means that the 3-GPA and the insulin sensitizing drug or insulin secretion stimulating drug are administered together, such as by co-administration, simultaneous administration or concomitant administration, at the same time or at different times, so long as the result is the systemic administration to the patient of 3-GPA and the insulin sensitizing drug or insulin secretion stimulating drug.

By "increasing endurance, stamina or exercise capacity" is meant an increase in the ability to participate in or maintain participation in physical activity, such as exercise.

By "mammal" is meant any of a class (Mammalia) of higher vertebrates comprising man and all other animals that nourish their young with milk secreted by mammary glands and have the skin usually more or less covered with hair. Especially included in this definition are human beings, whose endurance, stamina or exercise capacity is less than optimal. Such human and non-human animals are readily diagnosed by a physician or veterinarian of ordinary skill.

By "food" or "food product" is meant a material used in the body of a mammal to sustain growth, repair, and vital processes and to furnish energy. Especially preferred is a human food or food product. Both solid and liquid food products are included.

By "food additive" is meant a substance that is added to a food or food product.

By "nutritional supplement" is meant a substance that supplements a mammal's nutrition, such as vitamins.

NIDDM is a disease state that is frequently associated with obesity. Obesity is considered to be of importance in the development of NIDDM and in determining the severity of diabetes as it aggravates the insulin resistance that underlies NIDDM (E. F. Pfeiffer, and S. S. Fajans: Non-insulin-dependent diabetes mellitus. IDF Bulletin 34: 11–13, 1989). It is a common clinical observation that a weight gain of 10 to 15 lb presages the onset of NIDDM and that a similar weight loss results in significant improvement in plasma glucose of a patient with established diabetes (E. S. Horton, and B. Jeanrenaud: Obesity and diabetes mellitus, In: Ellenberg and Rifkin's Diabetes Mellitus, Theory and Practice, 4th Ed., edited by H. Rifkin and D. Porte, Jr., Elsevier, N.Y., 1990, page 457). Accordingly, weight reduction is considered to be the primary medical therapy for NIDDM patients (Physician's Guide to Non-Insulin-Dependent (Type II) Diabetes: Diagnosis and Treatment, supra, pages 2627; G. A. Bray: Obesity: An endocrine perspective. In: Endocrinology, Vol. 3, edited by L. J. DeGroot, Saunders, Philadelphia, 1989, page 2310).

In contrast, as can be seen from the American Diabetes Association Clinical Education Program, Physician's Guide to Insulin-Dependent (Type I) Diabetes: Diagnosis and Treatment, American Diabetes Association, Alexandria, Va. 1988, insulin-dependent diabetes mellitus (IDDM) patients may be of any age, are usually thin, and usually have abrupt onset of signs and symptoms with insulinopenia before age 30 years (Physician's Guide to Insulin-Dependent (Type I) Diabetes: Diagnosis and Treatment, supra, page 5). Usually, these patients have experienced significant weight loss before presentation (Physician's Guide to Insulin-Dependent (Type I) Diabetes: Diagnosis and Treatment, supra, page 3). Moreover, the primary defect in IDDM is inadequate insulin secretion by pancreatic beta cells, which results in hyperglycemia, polyuria, polydipsia, and weight loss. Their eventual absolute lack of insulin causes inability to store exogenous nutrients and uncontrolled release of stored nutrients from liver, muscle and adipose tissue (Physician's Guide to Insulin-Dependent (Type I) Diabetes: Diagnosis and Treatment, supra, page 9). In other words, it appears that patients with IDDM lose body fat and are unable to form new body fat without medical treatment. One goal of medical treatment is to cause a return to desirable body weight range in IDDM patients (Physician's Guide to Insulin-Dependent (Type I) Diabetes: Diagnosis and Treatment, supra, page 17).

For the treatment of NIDDM, drugs that are currently in use, e.g., insulin and sulfonylurea insulin secretion stimulators, may cause or exacerbate preexisting obesity (UK prospective study of therapies of maturity-onset diabetes. I. Effect of diet, sulphonylurea, insulin or biguanide therapy on fasting plasma glucose and body weight over one year. Diabetologia 24: 404–411, 1983). In particular, obese NIDDM patients who were treated for one year with insulin or the insulin secretion stimulators chlorpropamide or glyburide showed statistically significant increases in body weight in response to drug treatment (UK prospective study of therapies of maturity-onset diabetes. I. Effect of diet, sulphonylurea, insulin or biguanide therapy on fasting plasma glucose and body weight over one year. Diabetologia 24: 404–411, 1983). Thus their obesity was worsened by the conventional drug treatment for NIDDM. Animal studies indicate that insulin sensitizing drugs also cause or exacerbate obesity (Table 1).

The theoretical basis for increased adiposity in response to insulin or insulin secretion stimulators is well known: these drugs increase plasma levels of insulin and thereby stimulate fat synthesis and inhibit fat breakdown. As a consequence, body fat stores are increased (E. A. Newsholme and A. R. Leach: Biochemistry for the Medical Sciences, Wiley, N.Y., 1983, pages 348–350 and 629–631).

Insulin sensitizing drugs increase lipogenesis by enhancing the responsiveness of fat cells to endogenous insulin and, therefore, also result in increased body fat accumulation (A. Y. Chang, B. M. Wyse and B. J. Gilchrist: Ciglitazone, a new hypoglycemic agent. 1. Effect on glucose and lipid metabolism and insulin binding in the adipose tissue of C57BL/6J-ob/ob and ±/? mice. Diabetes 32: 839–845, 1983; Y. Sugiyama, S. Taketomi, Y. Shimura, H. Ikeda, and T. Fujita: Effects of pioglitazone on glucose and lipid metabolism in Wistar fatty rats. Arzneimittrschung 40: 263–267, 1990).

3-GPA decreases adiposity by decreasing the level of lipids stored in fat and liver tissue. The compound is therefore beneficial in the treatment of obesity in concert with NIDDM. The effect of 3-GPA is selective for lipid-rich tissues (e.g., epididymal fat and fatty liver of ob/ob mice) while muscle mass is unaffected or only minimally affected.

For example, 3-guanidinopropionic acid blocks weight gain in response to the insulin sensitizer pioglitazone hydrochloride (Table 1 below). This effect occurs without antagonizing the beneficial effect of pioglitazone hydrochloride on the hyperglycemic condition of diabetic KKAy mice. This represents an important therapeutic benefit since it allows amelioration of hyperglycemia without induction of obesity in NIDDM patients.

The dosage regimen for 3-guanidinopropionic acid effective to prevent or treat iatrogenic obesity will depend on the body weight of the patient. Typically, the effective amount of 3-guanidinopropionic acid is between 1 and 500 mg/kg body weight daily. The preferred amount is 5–100 mg/kg/day. (All of these amounts of 3-GPA are approximate.) The 3-GPA may be administered by any convenient route of administration, e.g., orally, parenterally, intranasally, intrarectally, or topically. The oral route is preferred. The above compositions may also be administered in a sustained release formulation. By "sustained release" is meant a formulation in which the drug becomes biologically available to the patient at a measured rate over a prolonged period. Such compositions are well-known in the art.

In the present invention, it has also been found that 3-guanidinopropionic acid (3-GPA) increases exercise tolerance in normal mice (FIG. 1 and Table 2 below). Thus the present invention may be useful in treating muscular dysfunction, such as post-poliomyelitis chronic muscle fatigue syndrome or muscular dystrophy, in treating chronic muscular weakness associated with advanced age or chronic immobilization, in treating lack of stamina or exercise capacity associated with the metabolic diseases described above, or in increasing endurance or exercise capacity in normal humans.

3-GPA also improved the survival rate of mice maintained in a low oxygen environment and therefore is beneficial in treating or preventing disease states involving tissue hypoxia, e.g., peripheral claudication and exercise intolerance in diabetic humans, and angina, myocardial infarction and stroke in diabetic and normal humans.

Furthermore, in a human patient suffering from a chronic disease, such as cancer, 3-GPA may be useful to prevent cachexia, which is a general wasting of the body during a chronic disease, and increase the survival time of such a patient. 3-GPA may also block the growth of tumors in a patient suffering from cancer. See, e.g., Y. Ohira et al., Biochim. Biophys. Acta., 1097(2): 117–122 (Sept. 23, 1991).

The dosage regimen for 3-guanidinopropionic acid effective to increase endurance, stamina or exercise capacity in a mammal will depend on the body weight of the patient. Typically, the effective amount of 3-guanidinopropionic acid is between 1 and 4000 mg/kg body weight daily. The preferred amount is 10–400 mg/kg/day, with 5–100 mg/kg/day being most preferred. (All of these amounts of 3-GPA are approximate.) The 3-GPA may be administered by any convenient route of administration, e.g., orally, parenterally, intranasally, intrarectally, or topically. The oral route is preferred. The above compositions may also be administered in a sustained release formulation, as described above.

For any of the above uses, for treating NIDDM as described in U.S. Pat. No. 5,132,324, which is hereby incorporated by reference herein, and for treating excess adiposity as described in U.S. Pat. No. 5,134,164, which is hereby incorporated by reference herein, 3-GPA may be administered orally in conventional foodstuffs. For example, 3-GPA may be dissolved in juices, such as orange juice, at a concentration of 75 mg/ml and taken by mouth. 3-GPA is adaptable to making a flavored dry mix which is constituted into a flavored beverage by simply adding water. These flavored mixes typically contain a viscosity inducing agent such as a gum or low molecular weight synthetic polymer; flavoring agents such as sucrose, aspartame or sodium saccharin; colorants; wetting agents or surfactants such as dioctyl sodium sulfosuccinate or sodium lauryl sulfate; agents to provide tartness and control acidity such as citric acid, ascorbic acid, potassium citrate or sodium citrate; flavorants such as lemon or orange; and preservatives such as BHA. Similarly, 3-GPA can be used as an additive to powdered food products, including pudding and pie filling mixes, gelatin, cake mixes, powdered eggs and powdered potatoes, instant breakfast drinks, gravies and sauces (e.g., Hollandaise), prepared cereal products (e.g., oatmeal, cream of wheat, hominy grits), and drink mixes (e.g., powdered fruit punches, powdered fruit drinks). Likewise, 3-GPA can be used in prepared foods themselves; for example, it can be used as an additive in cakes, pasta products, candy, cookies, confections, yogurts, including frozen yogurt products, ice cream and ice cream products and prepared meats (hamburger, sausages and the like).

A food product for human beings is most preferred. The amount of 3-GPA in the food product shall be that amount effective to increase endurance, stamina or exercise capacity in a patient in need thereof; to prevent or treat obesity in a non-insulin dependent diabetic (NIDDM) patient made susceptible to or experiencing obesity as a result of treatment with an insulin sensitizing drug or an insulin secretion stimulating drug; to treat excess adiposity in a patient in need thereof; or to treat NIDDM in a patient in need thereof. The approximate effective amount of 3-GPA for each of these uses is described above.

By way of illustration only and without intending to limit the disclosure herein, the amount of 3-GPA that may be most conveniently or practically incorporated into a liquid food product ranges from 1 to 200 mg/ml. Preferably the amount ranges from 70 to 200 mg/ml. For example, 3-GPA is soluble in water at room temperature at approximately 115 mg/ml. However, its solubility may be increased by acidification of the solution, such as with citric acid. The amount of 3-GPA that may be most conveniently or practically incorporated into a solid food product ranges from 1 to 500 mg/g. (All of these ranges of amounts of 3-GPA are approximate.) Variations in the amount of 3-GPA that may be incorporated into a food product, such as a liquid or solid food product, would be readily known to one of ordinary skill in the manufacture or formulation art.

DETAILED DESCRIPTION OF THE INVENTION

Figure 1:
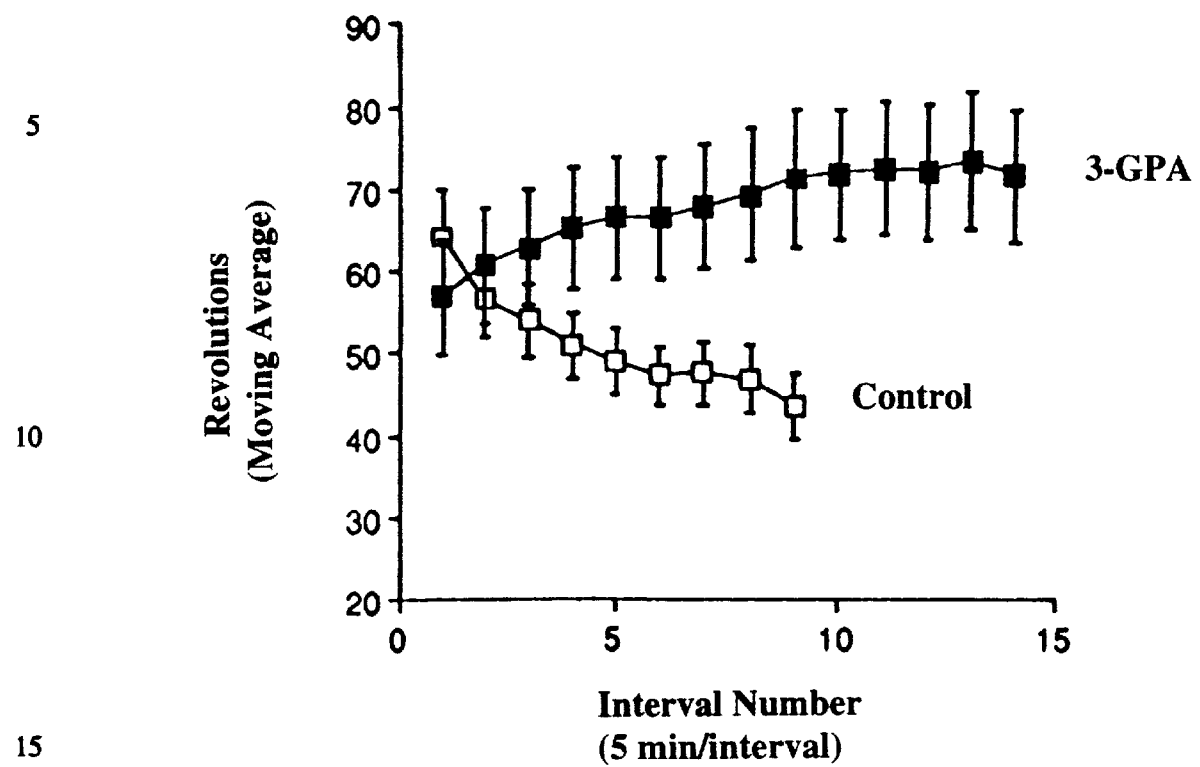

The present invention is seen more fully by the examples below:

EXAMPLE 1

Effect of 3-Guanidinopropionic Acid (3-GPA) on Body Weight in Obese, Diabetic Mice KKA$^y$ mice of both sexes, aged 3–4 months, were obtained from the Upjohn Laboratories diabetic rodent colony. Mice were individually caged and maintained at 21° C. using a 12 hour light-dark cycle. They were fed a diet of Purina 5015 mouse chow. 3-Guanidinopropionic acid was administered by admixing in milled chow. Control mice received milled chow that was unsupplemented.

The results of this study are presented in Table 1 below. It was found that 3-GPA antagonizes in a dose-dependent manner the weight gain that occurs in obese, diabetic KKAy mice that are treated with pioglitazone hydrochloride, an insulin sensitizing agent. The plasma glucose concentration was abnormally high in control mice, consistent with their diabetic state, but was decreased by pioglitazone. Combination of 3-GPA and pioglitazone did not impair the anti-diabetic action of the insulin sensitizer. This indicates that 3-GPA is of benefit in preventing or treating the obesity that results from use of an anti-diabetic drug by selectively blocking its undesirable obesity-promoting action without affecting its desirable anti-hyperglycemic action.

EXAMPLE 2

Effect of 3-Guanidinopropionic Acid (3-GPA) on Exercise Performance in Normal Mice C57BL6J mice, 105–150 days of age, were obtained from Charles River Laboratories (Portage, Mich.). Mice were individually caged and maintained at 21±1° C. using a 12 h light cycle. They were allowed free access to tap water and powdered Purina 5015 mouse chow containing 20 mg/g β-GPA, resulting in a daily intake of 4 g/kg body weight, or unsupplemented chow.

Briefly, mice were placed on a standard rodent exercise wheel, 22 inches in circumference, in a pan with water to a depth of approximately ¼ inch, so that it was necessary for them to run in order to remain above the water. When a mouse ceased running the wheel was tapped by the operator to stimulate further activity. The procedure was recorded on video tape to permit data analysis.

The results of this study are presented in Table 2 and FIG. 1 below. 3-Guanidinopropionic acid increased exercise performance when administered to C57BL6J mice in the diet for one month. The total distance run, the running time, and the latency to exhaustion were increased by 3-guanidinopropionic acid.

BRIEF DESCRIPTION OF FIG. 1

FIG. 1 is a plot of exercise endurance, measured as revolutions of a running wheel over a series of 5-minute intervals.

FORMULA CHART I

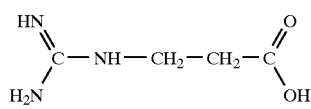

Effect of 3-guanidinopropionic acid (3-GPA) and pioglitazone HCl on plasma glucose and body weight in KKA$^y$ mice. Compounds were mixed in the chow at 2 or 5 mg/g for 3-GPA and 0.8 mg/g for pioglitazone hydrochloride for 14 days or unsupplemented chow was provided. KKA$^y$ mice are rodent models of NIDDM and obesity.

TABLE 1

Effect of 3-guanidinopropionic acid (3-GPA) and pioglitazone HCl on plasma glucose and body weight in KKA$^y$ mice. Compounds were mixed in the chow at 2 or 5 mg/g for 3–GPA and 0.8 mg/g for pioglitazone hydrochloride for 14 days or unsupplemented chow was provided. KKA$^y$ mice are rodent models of NIDDM and obesity.

| TREATMENT (3-GUANIDINO-PROPIONIC ACID (mg/g chow) | TREATMENT PIOGLITAZONE HCl (mg/g chow) | BODY WEIGHT (g) | plasma glucose (MG/DL) |
|---|---|---|---|
| 0 | 0 | 45.8 ± 0.9 | 432 ± 69 |
| 0 | 0.8 | 51.0 ± 0.8* | 302 ± 57 |
| 2 | 0.8 | 48.2 ± 0.8f | 299 ± 39 |
| 5 | 0.8 | 44.0 ± 1.3f | 241 ± 44* |

*P < 0.05, based on comparison to untreated controls.
f, P < 0.05, based on comparison with mice that received pioglitazone HCl, but no 3-GPA.

Effect of 3-guanidinopropionic acid (3-GPA) on running performance in C57BL6J mice. Compound were mixed in the chow at 20 mg/g for one month or unsupplemented chow was provided.

TABLE 2

Effect of 3-guanidinopropionic acid (3-GPA) on running performance in C57BL6J mice. Compound were mixed in the chow at 20 mg/g for one month or unsupplemented chow was provided.

|  | CONTROL | 3-Guanidinopropionic acid | P-VALUE |
|---|---|---|---|
| Running rat (0–45 min) (ft/min) | 16 ± 1 | 26 ± 3 | <0.05 |
| Total distance run (0–70 min) (ft) | 719 ± 65 | 1175 ± 136 | <0.05 |
| Total distance run (0–70 min) (ft) | 719 ± 65 | 1839 ± 205 | <0.05 |
| Latency to exhaustion (min) | 45 | >70 |  |

Running performance was measured in mice on an exercise wheel, 22 inches in circumference. The procedure was recorded on video tape in order to permit data analysis. Exhaustion was indicated by an abrupt decrease in running performance. In the case of 3-GPA treated mice exhaustion did not occur and the procedure was terminated by the technician after increased endurance was clearly demonstrated.

The effect of 3-guanidinopropionic acid (3-GPA) on exercise performance in C57BL6J mice is seen in FIG. 1. Data are shown as means±S.E.M. for revolutions of the exercise wheel. Data for each 5 min interval are expressed as moving averages calculated from t=0. N=5 mice/group. 3-GPA refers to mice administered chow supplemented with 20 mg/g 3-guanidinopropionic acid for 32 days.

I claim:

1. A liquid food product which comprises a foodstuff and at least 70 mg/ml 3-guanidinopropionic acid (3-GPA) or a pharmaceutically-acceptable salt thereof to:

a) increase the endurance, stamina or exercise capacity of a mammal;

b) treat exceeds adiposity in a mammal in need thereof; or c) treat non-insulin dependent diabetes mellitus in a mammal in need thereof.

2. The food product of claim 1 which comprises 70 to 200 mg/ml 3-GPA.

3. The food product of claim 1 or 2 wherein the foodstuff is orange juice.

* * * * *